(12) United States Patent
Minagawa

(10) Patent No.: US 9,963,565 B2
(45) Date of Patent: *May 8, 2018

(54) SURFACE MODIFICATION METHOD AND SURFACE-MODIFIED ELASTIC BODY

(71) Applicant: SUMITOMO RUBBER INDUSTRIES, LTD., Kobe-shi, Hyogo (JP)

(72) Inventor: Yasuhisa Minagawa, Kobe (JP)

(73) Assignee: SUMITOMO RUBBER INDUSTRIES, LTD., Kobe-Shi, Hyogo (JP)

( * ) Notice: Subject to any disclaimer, the term of this patent is extended or adjusted under 35 U.S.C. 154(b) by 0 days. days.

This patent is subject to a terminal disclaimer.

(21) Appl. No.: 14/857,528

(22) Filed: Sep. 17, 2015

(65) Prior Publication Data

US 2016/0096933 A1 Apr. 7, 2016

(30) Foreign Application Priority Data

Oct. 2, 2014 (JP) ................. 2014-204049

(51) Int. Cl.
 *C08J 7/18* (2006.01)
 *A61L 29/14* (2006.01)
(52) U.S. Cl.
 CPC .............. *C08J 7/18* (2013.01); *A61L 29/14* (2013.01); *A61L 2400/10* (2013.01); *A61L 2400/18* (2013.01); *C08J 2300/26* (2013.01); *C08J 2375/04* (2013.01); *C08J 2377/02* (2013.01)
(58) Field of Classification Search
 CPC ......... C08J 7/18; A61L 29/14; A61L 2400/00; A61L 2400/18; A61L 2420/02
 See application file for complete search history.

(56) References Cited

U.S. PATENT DOCUMENTS

| | | | |
|---|---|---|---|
| 3,418,066 A | 12/1968 | Caldwell et al. | |
| 5,100,689 A | 3/1992 | Goldberg et al. | |
| 5,154,727 A | 10/1992 | Dyer | |
| 5,340,879 A | 8/1994 | Audenaert et al. | |
| 5,453,467 A | 9/1995 | Bamford et al. | |
| 5,637,460 A | 6/1997 | Swan et al. | |
| 5,688,252 A | 11/1997 | Matsuda et al. | |
| 5,855,623 A | 1/1999 | English et al. | |
| 5,885,566 A | 3/1999 | Goldberg | |
| 5,889,073 A * | 3/1999 | Zhang ........................ | C08J 3/28 522/3 |
| 5,967,714 A | 10/1999 | Ottersbach et al. | |
| 6,001,894 A | 12/1999 | Ottersbach et al. | |
| 6,188,075 B1 | 2/2001 | Takayama et al. | |
| 6,203,856 B1 | 3/2001 | Ottersbach et al. | |
| 6,228,172 B1 | 5/2001 | Taylor et al. | |
| 6,358,557 B1 | 3/2002 | Wang et al. | |
| 6,808,738 B2 | 10/2004 | Ditizio et al. | |
| 7,348,055 B2 | 3/2008 | Chappa et al. | |
| 8,299,139 B1 | 10/2012 | Taranekar et al. | |
| 8,323,750 B2 | 12/2012 | Yang et al. | |
| 8,840,927 B2 | 9/2014 | Ditizio et al. | |
| 9,339,845 B2 | 5/2016 | Minagawa | |
| 9,469,736 B2 | 10/2016 | Minagawa | |
| 2002/0161065 A1 | 10/2002 | Ditizio et al. | |
| 2004/0086568 A1 | 5/2004 | Ditizio et al. | |
| 2004/0106732 A1 | 6/2004 | Tsuji et al. | |
| 2005/0137355 A1 | 6/2005 | Buckanin et al. | |
| 2006/0155057 A1 | 7/2006 | Hermeling et al. | |
| 2007/0003592 A1 | 1/2007 | Hissink | |
| 2007/0116971 A1 | 5/2007 | Yoshikawa et al. | |
| 2008/0016644 A1 | 1/2008 | Mizote et al. | |
| 2008/0103287 A1 | 5/2008 | Chino et al. | |

(Continued)

FOREIGN PATENT DOCUMENTS

| | | |
|---|---|---|
| CN | 101565489 A | 10/2009 |
| CN | 102382291 A | 3/2012 |

(Continued)

OTHER PUBLICATIONS

Ethanaminum, N,N,N-trimethyl-2-[(2-methyl-1-oxo-2-propen-1-yl) oxy]-chloride Product Information Inquiry Description from Jinan Haohua Industry Co., Ltd. found online on [Dec. 27, 20196]. Retrieved from Internet <URL://http://guide7932.guidechem.com/pro-show2436647.html>. (no date available).*
English machine translation of JP-2011-188908-A, published Sep. 29, 2011.
English machine translation of JP-7-100744-B2, published Nov. 1, 1995.
Allmér et al., "Surface Modification of Polymers. I. Vapour Phase Photografting with Acrylic Acid," Journal of Polymer Science: Part A: Polymer Chemistry, vol. 26, 1988, pp. 2099-2111.
International Search Report, dated Dec. 3, 2013, for International Application No. PCT/JP2013/074219.
International Search Report, dated Jul. 24, 2012, for International Application No. PCT/JP2012/064030.
U.S. Non-Final Office Action, dated May 8, 2015, for U.S. Appl. No. 13/756,837.
U.S. Non-Final Office Action, dated Oct. 20, 2014, for U.S. Appl. No. 13/756,837.

(Continued)

*Primary Examiner* — Sanza Mcclendon
(74) *Attorney, Agent, or Firm* — Birch, Stewart, Kolasch & Birch, LLP

(57) ABSTRACT

Provided are methods for surface-modifying a rubber vulcanizate or a thermoplastic elastomer, which enable surfaces with a chemically fixed lubricant to be produced instead of a resin coating which has drawbacks, such as that lubricity is reduced due to separation, peeling or the like of the coating during the movement within a vessel or tract. The present invention relates to a method for surface-modifying an object made of a rubber vulcanizate or a thermoplastic elastomer, the method including step 1 of forming polymerization initiation points on a surface of the object, and step 2 of radically polymerizing a halogen-containing deliquescent monomer, starting from the polymerization initiation points, by irradiation with ultraviolet light having a wavelength within the range of 300 to 400 nm to grow polymer chains on the surface of the object.

14 Claims, 1 Drawing Sheet

(56) References Cited

U.S. PATENT DOCUMENTS

| | | |
|---|---|---|
| 2008/0312377 A1 | 12/2008 | Schmidt et al. |
| 2009/0169715 A1 | 7/2009 | Dias et al. |
| 2009/0239089 A1 | 9/2009 | Agata et al. |
| 2010/0255336 A1 | 10/2010 | Zabinski |
| 2011/0160357 A1 | 6/2011 | Gerster et al. |
| 2011/0274940 A1 | 11/2011 | Kyomoto et al. |
| 2012/0021151 A1 | 1/2012 | Tatarka et al. |
| 2012/0100369 A1 | 4/2012 | Hanazawa et al. |
| 2013/0203883 A1 | 8/2013 | Minagawa |
| 2013/0274367 A1 | 10/2013 | Minagawa et al. |
| 2013/0310772 A1 | 11/2013 | Minagawa |
| 2014/0039084 A1 | 2/2014 | Minagawa |
| 2014/0128493 A1 | 5/2014 | Minagawa |
| 2015/0203612 A1 | 7/2015 | Minagawa |

FOREIGN PATENT DOCUMENTS

| | | |
|---|---|---|
| CN | 103242553 A | 8/2013 |
| EP | 0 872 512 A2 | 10/1998 |
| EP | 2 623 335 A2 | 8/2013 |
| EP | 2 664 627 A1 | 11/2013 |
| EP | 2 796 155 A1 | 10/2014 |
| EP | 2 894 191 A1 | 7/2015 |
| GB | 1120803 A | 7/1968 |
| GB | 1120804 A | 7/1968 |
| JP | 60-221410 A | 11/1985 |
| JP | 61-209667 A | 9/1986 |
| JP | 62-87163 A | 4/1987 |
| JP | 63-92658 A | 4/1988 |
| JP | 5-43634 A | 2/1993 |
| JP | 5-76590 A | 3/1993 |
| JP | 5-179055 A | 7/1993 |
| JP | 6-25450 A | 2/1994 |
| JP | 6-510322 A | 11/1994 |
| JP | 7-100744 B2 | 11/1995 |
| JP | 8-1793 A | 1/1996 |
| JP | 9-31361 A | 2/1997 |
| JP | 9-67457 A | 3/1997 |
| JP | 9-108359 A | 4/1997 |
| JP | 9-313594 A | 12/1997 |
| JP | 10-90500 A | 4/1998 |
| JP | 10-251350 A | 9/1998 |
| JP | 10-298320 A | 11/1998 |
| JP | 11-192305 A | 7/1999 |
| JP | 2000-273229 A | 10/2000 |
| JP | 2001-31871 A | 2/2001 |
| JP | 2001-46956 A | 2/2001 |
| JP | 2001-95621 A | 4/2001 |
| JP | 2002-145971 A | 5/2002 |
| JP | 2002-544346 A | 12/2002 |
| JP | 2003-2903 A | 1/2003 |
| JP | 2003-510378 A | 3/2003 |
| JP | 2004-528418 A | 9/2004 |
| JP | 2004-298220 A | 10/2004 |
| JP | 2005-516736 A | 6/2005 |
| JP | 2005-213516 A | 8/2005 |
| JP | 2005-523981 A | 8/2005 |
| JP | 2005-253538 A | 9/2005 |
| JP | 2007-77286 A | 3/2007 |
| JP | 2007-119563 A | 5/2007 |
| JP | 2007-145884 A | 6/2007 |
| JP | 2007-514861 A | 6/2007 |
| JP | 2007-202965 A | 8/2007 |
| JP | 2009-30074 A | 2/2009 |
| JP | 2009-518479 A | 5/2009 |
| JP | 2009-138169 A | 6/2009 |
| JP | 2009-226718 A | 10/2009 |
| JP | 2009-227842 A | 10/2009 |
| JP | 2010-23710 A | 2/2010 |
| JP | 2010-142537 A | 7/2010 |
| JP | 2010-142573 A | 7/2010 |
| JP | 2010-150349 A | 7/2010 |
| JP | 4523532 B2 | 8/2010 |
| JP | 2010-216964 A | 9/2010 |
| JP | 2011-42755 A | 3/2011 |
| JP | 2011-67362 A | 4/2011 |
| JP | 2011-188908 A | 9/2011 |
| JP | 2011-189562 A | 9/2011 |
| JP | 2011-208133 A | 10/2011 |
| JP | 2011-219520 A | 11/2011 |
| JP | 2011-241190 A | 12/2011 |
| JP | 2012-105579 A | 6/2012 |
| JP | 2012-162646 A | 8/2012 |
| JP | 2013-159629 A | 8/2013 |
| JP | 2013-159667 A | 8/2013 |
| JP | 2013-208777 A | 10/2013 |
| JP | 2013-237801 A | 11/2013 |
| JP | 2013-237802 A | 11/2013 |
| JP | 2014-31429 A | 2/2014 |
| JP | 2014-31430 A | 2/2014 |
| JP | 2014-108153 A | 6/2014 |
| WO | WO 93/05081 A1 | 3/1993 |
| WO | WO 03/068289 A1 | 8/2003 |
| WO | WO 03/093357 A1 | 11/2003 |
| WO | WO 2007/065721 A2 | 6/2007 |
| WO | WO 2007/072613 A1 | 6/2007 |
| WO | WO 2010/058848 A1 | 5/2010 |
| WO | WO 2010/131652 A1 | 11/2010 |
| WO | WO 2011/038483 A1 | 4/2011 |
| WO | WO 2012/091169 A1 | 7/2012 |
| WO | WO 2012/165525 A1 | 12/2012 |

OTHER PUBLICATIONS

U.S. Notice of Allowance, dated Dec. 26, 2014, for U.S. Appl. No. 13/956,974.
U.S. Office Action (Requirement for Restriction/Election), dated May 9, 2014, for U.S. Appl. No. 13/956,974.
U.S. Office Action, dated Apr. 17, 2015, for U.S. Appl. No. 13/775,451.
U.S. Office Action, dated Aug. 25, 2014, for U.S. Appl. No. 13/956,974.
U.S. Office Action, dated Jun. 24, 2015, for U.S. Appl. No. 14/118,136.
U.S. Office Action, dated Sep. 21, 2015, for U.S. Appl. No. 14/107,746.
International Search Report and English translation thereof, dated Jan. 21, 2014, for International Application No. PCT/JP2013/081090.
International Search Report and Written Opinion of the International Searching Authority, dated Jan. 20, 2015, for International Application No. PCT/JP2014/079947.
International Search Report, dated Aug. 19, 2014, for International Application No. PCT/JP2014/063268.
International Search Report, dated Feb. 25, 2014, for International Application No. PCT/JP2013/082409.
U.S. Office Action, dated Nov. 3, 2016, for U.S. Appl. No. 14/896,096.
"Fundamental of Polymer Chemistry and Physics," edited by Wuji Wei and etc., Chemical Industry Press, Oct. 2011, pp. 59-60 (4 pages total).
English translation of the Chinese Office Action, dated Sep. 22, 2017, for Chinese Application No. 201380044153.X.

* cited by examiner

SURFACE MODIFICATION METHOD AND SURFACE-MODIFIED ELASTIC BODY

TECHNICAL FIELD

The present invention relates to methods for surface modification which enable surfaces to exhibit lubricity when wetted; and surface-modified elastic bodies, such as medical devices or catheters, which have a surface at least partially modified by such a surface modification method.

BACKGROUND ART

Catheters used in the medical field or the like, such as vascular catheters and urethral catheters for urethral catheterization, and the like are inserted into blood vessels, digestive tracts, tracheae, bile ducts, or ureters and used in aqueous solutions such as blood or body fluids. They are thus required to be able to be smoothly inserted without damaging tissues.

In this context, a low friction lubricant is applied to the surface of a catheter, or the surface is coated with a lubricant layer, before use (see Patent Literatures 1 to 3). However, these methods have drawbacks in that the surfaces thus formed have insufficient lubricity, and that since the lubricants are not chemically fixed on the catheter surface, they are, for example, separated or peeled during the movement within a vessel or tract, so that the lubricity is reduced.

CITATION LIST

Patent Literature

Patent Literature 1: JP 2011-188908 A
Patent Literature 2: JP 2009-518479 T
Patent Literature 3: JP H07-100744 B

SUMMARY OF INVENTION

Technical Problem

The present invention aims to solve the aforementioned problems and provide methods for surface-modifying a rubber vulcanizate or a thermoplastic elastomer, which enable surfaces with a chemically fixed lubricant to be produced instead of a resin coating which has drawbacks, such as that lubricity is reduced due to separation, peeling or the like of the coating during the movement within a vessel or tract. The present invention also aims to provide surface-modified elastic bodies, such as medical devices (e.g. catheters), which have a surface at least partially modified by such a surface modification method.

Solution to Problem

The present invention relates to a method for surface-modifying an object made of a rubber vulcanizate or a thermoplastic elastomer, the method including: step 1 of forming polymerization initiation points on a surface of the object; and step 2 of radically polymerizing a halogen-containing deliquescent monomer, starting from the polymerization initiation points, by irradiation with ultraviolet light having a wavelength within the range of 300 to 400 nm to grow polymer chains on the surface of the object.

The present invention relates to a method for surface-modifying an object made of a rubber vulcanizate or a thermoplastic elastomer, the method including step I of radically polymerizing a halogen-containing deliquescent monomer in the presence of a photopolymerization initiator by irradiation with ultraviolet light having a wavelength within the range of 300 to 400 nm to grow polymer chains on a surface of the object.

The step 1 preferably includes adsorbing a photopolymerization initiator on the surface of the object, optionally followed by irradiation with ultraviolet light having a wavelength within the range of 300 to 400 nm, to form the polymerization initiation points from the photopolymerization initiator on the surface.

The photopolymerization initiator is preferably at least one of a benzophenone compound or a thioxanthone compound.

The method preferably includes inserting an inert gas into a reaction vessel, a reaction tube, and a reaction solution during or before the light irradiation, and polymerizing the monomer in an atmosphere replaced with the inert gas.

The halogen-containing deliquescent monomer is preferably a nitrogen-containing monomer. The nitrogen-containing monomer is preferably at least one of 2-(methacroyloxy)ethyl trimethylammonium chloride or 2-(acryloyloxy)ethyl trimethylammonium chloride.

Preferably, the (liquid) halogen-containing deliquescent monomer or a solution thereof contains a polymerization inhibitor, and is polymerized in the presence of the polymerization inhibitor. The polymerization inhibitor is preferably 4-methylphenol.

The polymer chains preferably each have a length of 10 to 5000 nm.

The present invention relates to a surface-modified elastic body, produced by the surface modification method.

The present invention relates to a surface-modified elastic body, produced by the surface modification method, the elastic body being required to have lubricity in the presence of water.

The present invention relates to a surface-modified elastic body, including a three-dimensional solid having a surface at least partially modified by the surface modification method.

The present invention also relates to a catheter, having a surface at least partially modified by the surface modification method.

Advantageous Effects of Invention

The methods for surface-modifying an object made of a rubber vulcanizate or a thermoplastic elastomer of the present invention include step 1 of forming polymerization initiation points on a surface of the object, and step 2 of radically polymerizing a halogen-containing deliquescent monomer, starting from the polymerization initiation points, by irradiation with ultraviolet light having a wavelength within the range of 300 to 400 nm to grow polymer chains on the surface of the object, or include step I of radically polymerizing a halogen-containing deliquescent monomer in the presence of a photopolymerization initiator by irradiation with ultraviolet light having a wavelength within the range of 300 to 400 nm to grow polymer chains on a surface of the object. Such methods enable the objects to have a surface with a lubricating polymer fixed thereon and, therefore, to get excellent lubricity and excellent lubricant durability after repeated movements, or in other words, durability that is so high that there will be little reduction in lubricity. Thus, by forming polymer chains on the surface of an object using the method, it is possible to produce a surface-modified elastic body, such as a surface-modified catheter, which is excellent in those properties.

DESCRIPTION OF EMBODIMENTS

Figure 1:
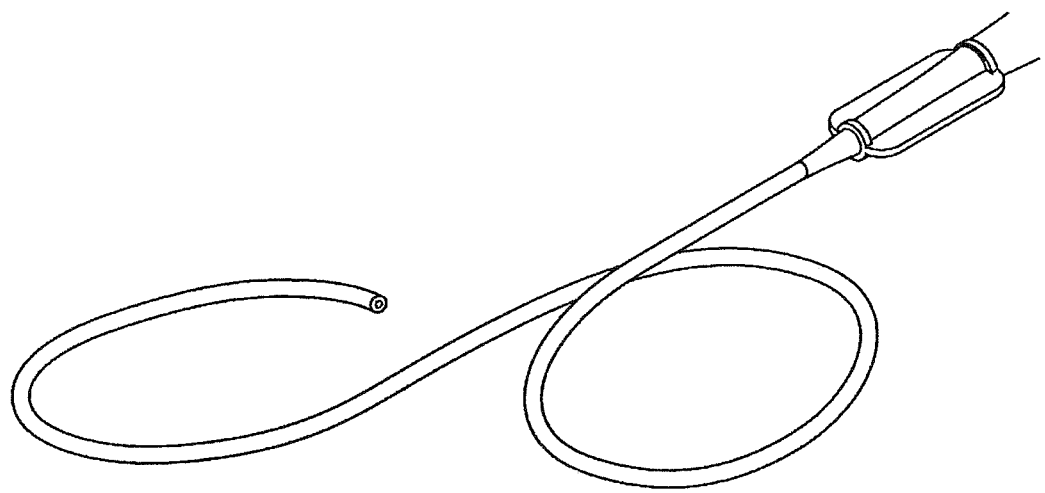
FIG. 1 is a schematic view of an example of a vascular catheter.
Figure 2:
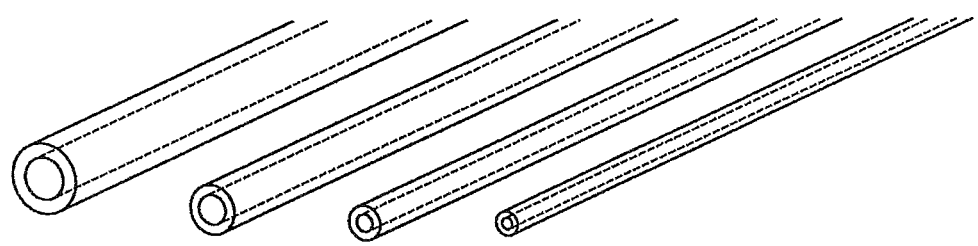
FIG. 2 is a schematic view showing examples of catheters with different diameters.

The present invention includes a method for surface-modifying an object made of a rubber vulcanizate or a thermoplastic elastomer, including step 1 of forming polymerization initiation points on a surface of the object, and step 2 of radically polymerizing a halogen-containing deliquescent monomer, starting from the polymerization initiation points, by irradiation with ultraviolet light having a wavelength within the range of 300 to 400 nm to grow polymer chains on the surface of the object.

In step 1, polymerization initiation points are formed on the surface of a molded rubber vulcanizate or a molded thermoplastic elastomer (the object to be modified). For example, the step 1 may be carried out by adsorbing a photopolymerization initiator on the surface of the object to form the polymerization initiation points, or by adsorbing a photopolymerization initiator on the surface of the object and then irradiating the surface with ultraviolet light having a wavelength within the range of 300 to 400 nm to form the polymerization initiation points from the photopolymerization initiator on the surface.

Examples of thermoplastic elastomers that can be used as the object to be modified include nylon, polyester, polyurethane, polypropylene, acrylonitrile-butadiene-styrene copolymer resin (ABS), fluororesins such as polytetrafluoroethylene, and dynamically crosslinked thermoplastic elastomers prepared from these elastomers. Examples of nylon include nylon 6, nylon 66, nylon 11, and nylon 12. The dynamically crosslinked thermoplastic elastomer is preferably obtained by dynamically crosslinking a halogenated butyl rubber in a thermoplastic elastomer. The thermoplastic elastomer used in this case is preferably nylon, polyurethane, polypropylene, styrene-isobutylene-styrene block copolymer (SIBS), or the like.

Examples of rubbers that can be used as the object to be modified include natural rubber, deproteinized natural rubber, styrene-butadiene rubber, polybutadiene rubber, polyisoprene rubber, silicone rubber, and butyl rubber and halogenated butyl rubber which have a degree of unsaturation of a few percent of isoprene units.

The conditions for vulcanization of the rubber may be appropriately set, and the vulcanization temperature of the rubber is preferably 140° C. or higher, more preferably 170° C. or higher, and still more preferably 175° C. or higher.

Examples of the photopolymerization initiator include carbonyl compounds, organic sulfur compounds such as tetraethylthiuram disulfide, persulfides, redox compounds, azo compounds, diazo compounds, halogen compounds, and photoreducing dyes. Preferred among these are carbonyl compounds.

Preferred among carbonyl compounds serving as photopolymerization initiators are benzophenone and derivatives thereof (benzophenone compounds). For example, suitable are benzophenone compounds represented by the following formula:

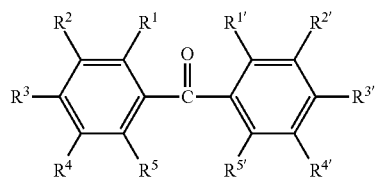

wherein $R^1$ to $R^5$ and $R^{1'}$ to $R^{5'}$ are the same as or different from one another and each represent a hydrogen atom, an alkyl group, a halogen (fluorine, chlorine, bromine, or iodine), a hydroxyl group, a primary to tertiary amino group, a mercapto group, or a hydrocarbon group that may contain an oxygen, nitrogen, or sulfur atom, and any two adjacent groups of $R^1$ to $R^5$ and $R^{1'}$ to $R^{5'}$ may be joined to each other to form a ring together with the carbon atoms to which they are attached.

Specific examples of the benzophenone compound include benzophenone, xanthone, 9-fluorenone, 2,4-dichlorobenzophenone, methyl o-benzoylbenzoate, 4,4'-bis(dimethylamino)benzophenone, and 4,4'-bis(diethylamino)benzophenone. Particularly preferred among these are benzophenone, xanthone, and 9-fluorenone because these compounds allow polymer brushes to be formed well.

The photopolymerization initiator may also suitably be a thioxanthone compound because it provides a high polymerization rate and can easily be adsorbed on and/or reacted with rubber or the like. For example, suitable are compounds represented by the following formula:

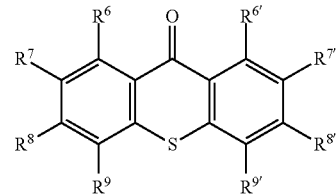

wherein $R^6$ to $R^9$ and $R^{6'}$ to $R^{9'}$ are the same as or different from one another and each represent a hydrogen atom, a halogen atom, or an alkyl, cyclic alkyl, aryl, alkenyl, alkoxy, or aryloxy group.

Examples of thioxanthone compounds represented by the above formula include thioxanthone, 2-isopropylthioxanthone, 4-isopropylthioxanthone, 2,3-diethylthioxanthone, 2,4-diethylthioxanthone, 2,4-dichlorothioxanthone, 2-methoxythioxanthone, 1-chloro-4-propoxythioxanthone, 2-cyclohexylthioxanthone, 4-cyclohexylthioxanthone, 2-vinylthioxanthone, 2,4-divinylthioxanthone, 2,4-diphenylthioxanthone, 2-butenyl-4-phenylthioxanthone, and 2-p-octyloxyphenyl-4-ethylthioxanthone. Preferred among these are those which are substituted at one or two, especially two, of $R^6$ to $R^9$ and $R^{6'}$ to $R^{9'}$ with alkyl groups. More preferred is 2,4-diethylthioxanthone.

The adsorption of a photopolymerization initiator such as a benzophenone or thioxanthone compound on the surface of the object to be modified may be carried out as follows. In the case of using a benzophenone or thioxanthone compound, for example, the benzophenone or thioxanthone compound is dissolved in an organic solvent to prepare a solution; a surface portion of the object to be modified is treated with this solution so that the compound is adsorbed on the surface portion; and, if necessary, the organic solvent is dried and evaporated off, whereby polymerization initiation points are formed. The surface-treating method may be any method that allows the solution of the benzophenone or thioxanthone compound to be brought into contact with the surface of the object. Suitable methods include applying or spraying the benzophenone or thioxanthone compound solution onto the surface; or, alternatively, immersing the surface into the solution. When only a part of the surface needs to be modified, it is sufficient to adsorb the photopolymerization initiator only on the necessary part of the surface. In this case, for example, application or spraying of the solution is suitable. Examples of the solvent include methanol, ethanol, acetone, benzene, toluene, methyl ethyl ketone, ethyl acetate, and THF. Acetone is preferred because it does not swell the object and it can be rapidly dried and evaporated off.

As described, after the photopolymerization initiator is adsorbed on the surface of the object, the surface may then be irradiated with ultraviolet light having a wavelength within the range of 300 to 400 nm to form the polymerization initiation points from the photopolymerization initiator on the surface. This irradiation with ultraviolet light can be carried out by known methods. For example, it may be carried out by the method used in the irradiation with ultraviolet light in step 2 described later.

In step 2, a halogen-containing deliquescent monomer is radically polymerized starting from the polymerization initiation points formed in step 1, by irradiation with ultraviolet light having a wavelength within the range of 300 to 400 nm to grow polymer chains on the surface of the object.

The halogen-containing deliquescent monomer refers to a monomer that contains a halogen atom in the molecule and has deliquescent properties, that is, a halogen atom-containing monomer having properties of spontaneously absorbing moisture (water vapor) from the air and forming an aqueous solution. The halogen-containing deliquescent monomer is not particularly limited as long as it has such properties. The halogen-containing deliquescent monomers may be used alone or in combinations of two or more.

In view of lubricity and its durability, the halogen-containing deliquescent monomer may suitably be a nitrogen-containing monomer (halogen- and nitrogen-containing deliquescent monomer). Specific preferred examples of such monomers include compounds represented by the following formula (I):

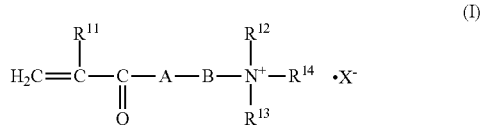

(I)

wherein A represents an oxygen atom or NH; B represents a C1-C4 alkylene group; $R^{11}$ represents a hydrogen atom or a methyl group; $R^{12}$, $R^{13}$, and $R^{14}$ are the same as or different from one another and each represent a C1-C4 alkyl group; and $X^-$ represents a halogen ion.

A is preferably an oxygen atom. B may be a linear or branched alkylene group such as a methylene, ethylene, or propylene group. Among these, a methylene or ethylene group is preferred. Each of $R^{12}$ to $R^{14}$ may be a linear or branched alkyl group such as a methyl, ethyl or propyl group. Among these, a methyl or ethyl group is preferred. X (halogen atom) may be fluorine, chlorine, bromine or the like. Among these, chlorine is preferred.

Examples of nitrogen-containing monomers represented by the formula (I) include 2-(methacroyloxy)ethyl trimethylammonium chloride (2-(methacroyloxy)ethyl trimethylaminium chloride), 2-(acryloyloxy)ethyl trimethylammonium chloride (2-(acryloyloxy)ethyl trimethylaminium chloride), 2-(methacroyloxy)ethyl dimethylethylammonium chloride (2-(methacroyloxy)ethyl dimethylethylaminium chloride), and 2-(acryloyloxy)ethyl dimethylethylammonium chloride (2-(acryloyloxy)ethyl dimethylethylaminium chloride).

In addition to the halogen-containing deliquescent monomer, the following monomers may be used to form polymer chains: alkali metal-containing monomers such as alkali metal salts of acrylic acid (e.g. sodium acrylate, potassium acrylate) and alkali metal salts of methacrylic acid (e.g. sodium methacrylate, potassium methacrylate); and zwitterionic monomers such as carboxybetaines, sulphobetaines, and phosphobetaines.

The radical polymerization of a halogen-containing deliquescent monomer in step 2 may be carried out as follows: A (liquid) halogen-containing deliquescent monomer or a solution thereof is applied (sprayed) onto the surface of the object on which a benzophenone or thioxanthone compound or the like has been adsorbed, or alternatively, the object is immersed in a (liquid) halogen-containing deliquescent monomer or a solution thereof; and the object is then irradiated with ultraviolet light to allow radical polymerization (photo-radical polymerization) of the monomer to proceed, whereby polymer chains are grown on the surface of the object. After the application, the surface of the object may also be covered with a sheet of transparent glass, PET, polycarbonate or the like, followed by irradiating the covered surface with ultraviolet light to allow radical polymerization (photo-radical polymerization) of the monomer to proceed, whereby polymer chains are grown on the surface of the object.

The solvent for application (spraying), the method for application (spraying), the method for immersion, the conditions for irradiation, and the like may be conventionally known materials or methods. The solution of the monomer may be an aqueous solution, or a solution in an organic solvent that does not dissolve the photopolymerization initiator (e.g. benzophenone or thioxanthone compound) used. Furthermore, the (liquid) monomer or a solution thereof may contain a known polymerization inhibitor such as 4-methylphenol.

In the present invention, radical polymerization of the halogen-containing deliquescent monomer is allowed to proceed by light irradiation after the (liquid) halogen-containing deliquescent monomer or a solution thereof is applied to the surface, or after the surface is immersed in the (liquid) halogen-containing deliquescent monomer or a solution thereof. Here, ultraviolet light sources with an emission wavelength mainly in the ultraviolet region, such as high-pressure mercury lamps, metal halide lamps, and LED lamps, can be suitably used. The light dose may be appropriately chosen in view of polymerization time and uniform progress of the reaction. Moreover, in order to prevent inhibition of polymerization due to active gas such as oxygen in the reaction vessel and the reaction tube, oxygen is preferably removed from the reaction vessel, the reaction tube, and the reaction solution during or before the light irradiation. To this end, appropriate operations may be performed. For example, an inert gas such as nitrogen gas or argon gas is inserted into the reaction vessel, the reaction tube, and the reaction solution to discharge active gas such as oxygen from the reaction system and replace the atmosphere in the reaction system with the inert gas. Furthermore, in order to prevent inhibition of the reaction due to oxygen or the like, for example, a measure may appropriately be taken in which an ultraviolet light source is placed such that an air layer (oxygen content: 15% or higher) does not exist between the reaction vessel made of glass, plastics or the like and the reaction solution or the object.

The ultraviolet light has a wavelength within the range of 300 to 400 nm. Such a wavelength enables polymer chains to be formed well on the surface of the object. Examples of light sources that can be used include high-pressure mercury lamps, LEDs with a center wavelength of 365 nm, and LEDs with a center wavelength of 375 nm. More preferred is irradiation with LED light having a wavelength within the range of 355 to 380 nm. In particular, LEDs or the like having a center wavelength of 365 nm, which is close to the excitation wavelength (366 nm) of benzophenone, are preferred in view of efficiency. Light with a wavelength of shorter than 300 nm may break and damage the molecules of the object. Thus, light having a wavelength of 300 nm or longer is preferred, and light having a wavelength of 355 nm or longer is more preferred because it produces very little damage to the object. Light having a wavelength of longer than 400 nm, however, is less likely to activate the photopolymerization initiator, with the result that the polymerization reaction is not allowed to easily proceed. Thus, light having a wavelength of 400 nm or shorter is preferred. Although LED light is suitable in that it is in a narrow wavelength range and does not contain light with other wavelengths than the center wavelength, a mercury lamp or the like can also achieve similar effects to LED light if a filter is used to block light having a wavelength of shorter than 300 nm.

The present invention also relates to a method for surface-modifying an object made of a rubber vulcanizate or a thermoplastic elastomer, including step I of radically polymerizing a halogen-containing deliquescent monomer in the presence of a photopolymerization initiator by irradiation with ultraviolet light having a wavelength within the range of 300 to 400 nm to grow polymer chains on a surface of the object. Specifically, a halogen-containing deliquescent monomer is radically polymerized using a photopolymerization initiator by irradiation with ultraviolet light to form polymer chains, whereby a surface-modified elastic body can be produced in which a polymer layer is formed on the surface of the object. The object to be modified, the photopolymerization initiator, and the halogen-containing deliquescent monomer used in step I may be as described hereinabove.

For example, the step I may be carried out by contacting the surface of the object with a photopolymerization initiator and a halogen-containing deliquescent monomer, and then irradiating the surface with LED light having a wavelength within the range of 300 to 400 nm to form polymerization initiation points from the photopolymerization initiator while radically polymerizing the halogen-containing deliquescent monomer, starting from the polymerization initiation points, to grow polymer chains.

The radical polymerization of a halogen-containing deliquescent monomer in step I may be carried out as follows: A (liquid) halogen-containing deliquescent monomer or a solution thereof which contains a photopolymerization initiator such as a benzophenone or thioxanthone compound is applied (sprayed) onto the surface of the object, or alternatively, the object is immersed in a (liquid) halogen-containing deliquescent monomer or a solution thereof which contains a photopolymerization initiator; and the object is then irradiated with ultraviolet light to allow radical polymerization (photo-radical polymerization) of the monomer to proceed, whereby polymer chains are grown on the surface of the object. As described above, for example, the surface of the object may also be covered with a sheet of transparent glass, PET, polycarbonate or the like, followed by irradiating the covered surface with ultraviolet light. Here, the solvent for application (spraying), the method for application (spraying), the method for immersion, the conditions for irradiation, and the like may be materials or methods as described hereinabove.

The polymer chains formed in step 2 or step I preferably each have a length of 10 to 5000 nm, more preferably 100 to 5000 nm. Polymer chains shorter than 10 nm tend not to provide good lubricity. Polymer chains longer than 5000 nm cannot be expected to provide further improved lubricity, while they tend to lead to an increase in the cost of raw materials because the monomer used is expensive. In addition, in such cases, surface patterns generated by the surface treatment tend to be visible to the naked eye and thereby spoil the appearance and decrease sealing properties.

In step 2 or step I, two or more kinds of monomers may be radically polymerized simultaneously. Moreover, multiple kinds of polymer chains may be grown on the surface of the object. In the surface modification methods of the present invention, the polymer chains may be cross-linked to one another. In this case, the polymer chains may be cross-linked to one another by ionic crosslinking, crosslinking by a hydrophilic group containing an oxygen atom, or crosslinking by a halogen group such as iodine.

The surface modification methods can be applied to rubber vulcanizates or thermoplastic elastomers to produce surface-modified elastic bodies. For example, surface-modified elastic bodies that are excellent in lubricity in the presence of water can be obtained. Moreover, the methods may be applied to at least a part of a three-dimensional solid (e.g. elastic body) to obtain a surface-modified elastic body with modified properties. Furthermore, preferred examples of such surface-modified elastic bodies include polymer brushes. The term "polymer brush" means an assembly of graft polymer molecules obtained in the "grafting from" approach by surface-initiated living radical polymerization. Moreover, the graft chains are preferably oriented in a direction substantially vertical to the surface of the object because, in such a case, the entropy is reduced and thus the molecular mobility of the graft chains is reduced, which provides lubricity. Furthermore, semidilute or concentrated brushes having a brush density of 0.01 chains/nm$^2$ or higher are preferred.

The surface modification methods may also be applied to rubber vulcanizates or thermoplastic elastomers to produce medical devices, such as catheters, at least part of whose surface is modified. The modification is preferably applied to at least a surface portion of the medical device (e.g. catheter) that requires lubricity, and it may be applied to the entire surface.

EXAMPLES

The present invention is more specifically described with reference to examples below. The present invention is, however, not limited to these examples.

Example 1

A 3 wt % solution of benzophenone in acetone was applied to the surface of a thermoplastic elastomer tube made of nylon 12 so that benzophenone was adsorbed on the surface, followed by drying. Then, the tube was irradiated with LED light (5 mW/cm$^2$) with a wavelength of 365 nm for five minutes while the tube was rotated such that the entire surface was irradiated.

Subsequently, the tube was immersed in an aqueous solution of 2-(methacroyloxy) ethyl trimethylammonium chloride (1.25 M) in a glass reaction vessel. The reaction vessel was sealed with a rubber stopper, and argon gas was inserted and allowed to bubble through the solution for 120 minutes to remove oxygen. The glass reaction vessel was irradiated with LED light (5 mW/cm$^2$) with a wavelength of 365 nm for 210 minutes while being rotated. Thus, radical polymerization was carried out to grow polymer chains on the surface of the nylon tube, whereby a surface-modified elastic body (polymer brush) was prepared.

Example 2

A 3 wt % solution of benzophenone in acetone was applied to the surface of a thermoplastic elastomer tube made of nylon 12 so that benzophenone was adsorbed on the surface, followed by drying.

Then, the tube was immersed in an aqueous solution of 2-(methacroyloxy) ethyl trimethylammonium chloride (1.25 M) in a glass reaction vessel. The reaction vessel was sealed with a rubber stopper, and argon gas was inserted and allowed to bubble through the solution for 120 minutes to remove oxygen. The glass reaction vessel was irradiated with LED light (5 mW/cm$^2$) with a wavelength of 365 nm for 210 minutes while being rotated. Thus, radical polymerization was carried out to grow polymer chains on the surface of the nylon tube, whereby a surface-modified elastic body (a polymer brush) was prepared.

Example 3

A 3 wt % solution of 2,4-diethylthioxanthone in acetone was applied to the surface of a thermoplastic elastomer tube made of nylon 12 so that 2,4-diethylthioxanthone was adsorbed on the surface, followed by drying.

Then, the tube was immersed in an aqueous solution of 2-(methacroyloxy) ethyl trimethylammonium chloride (1.25 M) in a glass reaction vessel. The reaction vessel was sealed with a rubber stopper, and argon gas was inserted and allowed to bubble through the solution for 120 minutes to remove oxygen. The glass reaction vessel was irradiated with LED light (5 mW/cm$^2$) with a wavelength of 365 nm for 100 minutes while being rotated. Thus, radical polymerization was carried out to grow polymer chains on the surface of the nylon tube, whereby a surface-modified elastic body (a polymer brush) was prepared.

Example 4

A surface-modified elastic body (a polymer brush in which polymer chains were grown on the surface of a polyurethane tube) was prepared in the same manner as in Example 1, except that a polyurethane tube was used instead of the nylon tube in Example 1.

Comparative Example 1

A tube made of nylon 12 was used as it was.

Comparative Example 2

Used was a tube made of nylon 12, the surface of which was coated with a 5% solution of methyl vinyl ether-maleic anhydride (GANTREZ-AN 16, produced by IPS) in methanol. It should be noted that nylon 12 is a material often used for vascular catheters, and methyl vinyl ether-maleic anhydride is a typical lubricant to provide the surface with lubricity.

The surface-modified elastic bodies prepared in the examples and the comparative examples were evaluated as follows.

(Length of Polymer Chain)

To determine the length of the polymer chain formed on the surface of the tube, a cross section of the tube with polymer chains was measured with a SEM at an accelerating voltage of 15 kV and a magnification of 1000 times. The thickness of the polymer layer photographed was determined and used as the length of the polymer chain.

(Lubricity)

Water was applied to the surface of the tube, and the sliding properties of the surface were then subjectively evaluated by touching with a human finger. The subjective evaluation was carried out by ten persons according to the following rating scale of 1-5: a rating of 5 corresponds to a tube with good sliding properties and a rating of 1 corresponds to a tube with so poor sliding properties that the finger never slides on the surface. The average rating was calculated.

(Lubricant Durability)

After water was applied to the surface of the tube, the tube was held between fingers and moved by sliding on the fingers. This cycle was repeated 100 times. Then, the subjective evaluation was again carried out by ten persons according to the rating scale for lubricity, and the average rating and the rate of decrease from the initial lubricity were calculated.

TABLE 1

|  | Example 1 | Example 2 | Example 3 | Example 4 | Comparative Example 1 | Comparative Example 2 |
| --- | --- | --- | --- | --- | --- | --- |
| Length of polymer chain (nm) | 2100 | 2400 | 2500 | 1500 | — | — |
| Lubricity | 4.8 | 4.9 | 5 | 4.5 | 1 | 4.2 |
| Durability | 4.75 | 4.85 | 4.9 | 4.45 | 1 | 2.4 |
| Rate of decrease | 1% | 1% | 2% | 2% | 0% | 43% |

Table 1 shows that the surfaces of the tubes of the examples had high lubricity, good durability, and quite a low rate of decrease in lubricity. In contrast, the untreated tube of Comparative Example 1 exhibited quite poor lubricity; the commonly used product of Comparative Example 2 had moderately high initial lubricity, but exhibited low durability and quite a high rate of decrease in lubricity.

These results demonstrated that by forming polymer chains on the surface of a vascular catheter or the like using a halogen-containing deliquescent monomer such as 2-(methacroyloxy)ethyl trimethylammonium chloride or 2-(acryloyloxy)ethyl trimethylammonium chloride, it is possible to simultaneously provide it with sufficient lubricity and lubricant durability.

The invention claimed is:

1. A method for growing polymer chains from a surface of an object made of a rubber vulcanizate or a thermoplastic elastomer, the method comprising:
    step 1 of forming polymerization initiation points on the surface of the object; and
    step 2 of growing the polymer chains from the surface of the object by radically polymerizing a halogen-containing deliquescent monomer, starting from the polymerization initiation points, by irradiation with ultraviolet light having a wavelength within the range of 300 to 400 nm.

2. A method for growing polymer chains on a surface of an object made of a rubber vulcanizate or a thermoplastic elastomer, the method comprising
    step I of growing the polymer chains from the surface of the object by radically polymerizing a halogen-containing deliquescent monomer in the presence of a photopolymerization initiator by irradiation with ultraviolet light having a wavelength within the range of 300 to 400 nm.

3. The method according to claim 1,
    wherein the step 1 comprises adsorbing a photopolymerization initiator on the surface of the object, optionally followed by irradiation with ultraviolet light having a wavelength within the range of 300 to 400 nm, to form the polymerization initiation points from the photopolymerization initiator on the surface.

4. The method according to claim 3,
    wherein the photopolymerization initiator is at least one of a benzophenone compound or a thioxanthone compound.

5. The method according to claim 1,
    wherein the method comprises inserting an inert gas into a reaction vessel, a reaction tube, and a reaction solution during or before the light irradiation, and polymerizing the monomer in an atmosphere replaced with the inert gas.

6. The method according to claim 1,
    wherein the halogen-containing deliquescent monomer is a nitrogen-containing monomer.

7. The method according to claim 6,
    wherein the nitrogen-containing monomer is at least one of 2-(methacroyloxy)ethyl trimethylammonium chloride or 2-(acryloyloxy)ethyl trimethylammonium chloride.

8. The method according to claim 1,
    wherein the (liquid) halogen-containing deliquescent monomer or a solution thereof contains a polymerization inhibitor, and is polymerized in the presence of the polymerization inhibitor.

9. The method according to claim 8,
    wherein the polymerization inhibitor is 4-methylphenol.

10. The method according to claim 1,
    wherein the polymer chains each have a length of 10 to 5000 nm.

11. A surface-modified elastic body, produced by the method according to claim 1.

12. A surface-modified elastic body, produced by the method according to claim 1, the elastic body being required to have lubricity in the presence of water.

13. A surface-modified elastic body, comprising a three-dimensional solid having a surface at least partially modified by the method according to claim 1.

14. A catheter, having a surface at least partially modified by the method according to claim 1.

* * * * *